United States Patent [19]

Shah et al.

[11] 4,131,651

[45] Dec. 26, 1978

[54] TREATMENT OF DRY EYE

[75] Inventors: Dinesh O. Shah, Gainesville, Fla.; Murray J. Sibley, Berkeley, Calif.

[73] Assignee: Barnes-Hind Pharmaceuticals, Inc., Sunnyvale, Calif.

[21] Appl. No.: 844,555

[22] Filed: Oct. 25, 1977

[51] Int. Cl.$^2$ .............................................. A61K 31/74
[52] U.S. Cl. ................................................... 424/78
[58] Field of Search .................................. 424/78, 80

[56] References Cited

U.S. PATENT DOCUMENTS

| | | | |
|---|---|---|---|
| 2,861,920 | 11/1958 | Dale et al. | 424/80 |
| 3,311,577 | 3/1967 | Rankin | 424/80 |
| 3,843,782 | 10/1974 | Krezanoski et al. | 424/78 |
| 3,845,201 | 10/1974 | Haddad et al. | 424/273 |
| 3,856,919 | 12/1974 | Rankin | 424/80 |
| 3,927,205 | 12/1975 | Ohno et al. | 424/80 |

FOREIGN PATENT DOCUMENTS 1090492  11/1967  United Kingdom.

*Primary Examiner*—Stanley J. Friedman
*Assistant Examiner*—D. W. Robinson
*Attorney, Agent, or Firm*—Townsend and Townsend

[57] ABSTRACT

Methods and compositions are provided for the treatment of dry eye and discontinuous tear films. The ophthalmic solution for maintaining a continuous tear film employs a combination of hydroxyalkylcellulose and polyvinyl alcohol in a predetermined ratio in an aqueous isotonic medium.

2 Claims, No Drawings

TREATMENT OF DRY EYE

BACKGROUND OF THE INVENTION

Field of the Invention

In many situations, it is found that the lachrymal film is discontinuous. This can be a result of weak lachrymal films, as inadequate rate of blinking, or with some users, wearing of contact lenses. There is, therefore, a need to provide a synthetic tear which can act as a tear substitute for dry eye syndromes. In addition, solutions which would provide stable ocular films could be used for prolonging the precorneal tear film retention of drugs instilled in liquid ophthalmic vehicles and for the wetting and cushioning of contact lenses.

Description of the Prior Art

Benedetto, Shah and Kaufman, Investigative Ophthalmology 14, 887 (1975) describes testing of hydroxypropylmethylcellulose and polyvinyl alcohol to prolong precorneal tear films.

SUMMARY OF THE INVENTION

A combination of hydroxyalkylcellulose and polyvinyl alcohol in about a 4 to 1 weight ratio is provided for use in aqueous solutions for treatment of dry eye and maintenance of stable lachrymal films. The aqueous compositions are preferably employed as isotonic solutions, having a viscosity in the range of about 5–70cs at 25° C.

DESCRIPTION OF THE SPECIFIC EMBODIMENTS

Novel compositions are provided employing in combination hydroxyalkylcellulose and polyvinyl alcohol, with the hydroxyalkylcellulose in the range of about 70 to 85 weight percent, preferably 75 to 85 weight percent, and more preferably 80 weight percent and reciprocally the polyvinyl alcohol in about 15 to 30, more usually 15 to 25 and preferably 20 weight percent. The polymer combination is normally employed as a uniform aqueous dispersion, normally a solution, which may be provided as a concentrate or as a solution for physiological use. The weight percent of the polymer combination will therefore vary from about 0.1 to 10, more usually from about 0.2 to 6 weight percent. For use in the eye, the concentration will generally vary from about 0.1 to 2.5 weight percent, more usually from about 0.5 to 2 weight percent, preferably from about 0.75 to 1.5 weight percent. Generally, those solutions which find use in the eye will have viscosities in the range of about 5–70cs, more usually 5–60cs and preferably from about 10 to 50cs at 25° C. The solutions employed for treatment, when instilled into the conjunctival sac stabilizes or maintains a continuous lachrymal fluid film covering the eye.

In addition to the active ingredients of this invention, other materials will normally be included in the aqueous vehicle. Preferably, the composition is provided as isotonic, particularly employing sodium chloride. Generally, from about 0.4 to 1.4 weight percent sodium chloride, normally from about 0.7 to 1.1 weight percent sodium chloride will be employed.

Other additives may also be included, such as physiologically acceptable preservatives, disinfectants, buffers, and the like, depending upon the function of the medium and the presence of drugs for eye medication.

Illustrative preservatives and disinfectants include chlorobutanol, thimerosal, chlorhexidine, benzalkonium chloride, phenylmercuric acetate, phenylmercuric nitrate and methyl and propylparabens. The total amount of disinfectants and preservatives will generally be in the range of about 0.0005 to 1 weight percent, more usually from about 0.001 to 0.5 weight percent.

The pH of the medium will generally be within an acceptable physiological range from about 5.5 to 8.5 usually from about 6.5 to 7.5. This can be achieved by the addition of a physiologically acceptable base or acid, e.g. sodium hydroxide or hydrochloric acid, or by employing such buffers as carbonate, borate, etc. When the solution is provided as a concentrate, all of the amounts will normally be increased from about 1.5 to 6 times, more usually from about 1.5 to 4 times the amount desired in the final solution.

The hydroxylalkylcellulose which is employed will have alkylene groups of from 2 to 3 carbon atoms, more usually of 2 carbon atoms, i.e. ethylene. Normally, there will be on the average from about 1 to 3 hydroxyalkyl per anhydroglucosidemoiety, more usually from about 1.5 to 3.0 groups, and preferably from about 2.25 to 2.75 groups, and more preferably 2.5 groups. The viscosity average molecule weight of the hydroxyalkylcellulose will generally be in the range of about 1 to $10 \times 10^5$. The viscosity of the polymer will generally be in the range of about 3,000 to 8,000, more usually about 4,500 to 6,500 cps (2 wt % aqueous solution, Brookfield Viscosity, 25° C.).

The polyvinyl alcohol which is employed will generally have not more than about 20, preferably not more than about 15 mole percent vinyl acetate momoner, and usually at least about 2 mole percent vinyl acetate monomer. The polyvinyl alcohol polymer will normally have a viscosity of about 1 to 20, usually about 2 to 10 and preferably about 4 to 6 cs using a 4% w/v solution, (ASTM 882). The viscosity average molecular weight will usually be in the range of about 3 to $30 \times 10^4$.

EXPERIMENTAL

A number of tests were performed which relate to the stability of ocular films. The following tables indicates the results obtained with aqueous solutions of polyvinyl alcohol and hydroxyethylcellulose in varying proportions, both within and without the ranges of the subject invention.

| Aqueous 1% (w/v) -PVA-HEC Mixtures | | Film Thickness Weight Technique[3] | Film Thickness by Draining Technique[4] | Drainage Time[4] | Dewetting Time[5] | Surface Viscosity[6] | Relative Viscosity[7] | Vertical Film Climbing Rate[8] | Surface Tension |
|---|---|---|---|---|---|---|---|---|---|
| %PVA(w/w)[1] | %HEC(w/w)[2] | μ | μ | min | hr | (poise) | (t/t_o) | | (dyne/cm.) |
| 100 | 0 | 10.4 | 10.3 | 3.65 | 5.0 | 0.0093 | 1.45 | 11.8 | 42.0 |
| 80 | 20 | 11.6 | — | — | — | — | 1.75 | — | 42.0 |
| 60 | 40 | 12.5 | 11.7 | — | — | — | 2.1 | — | 42.0 |
| 40 | 60 | 13.2 | — | 4.1 | 5.0 | 0.024 | 2.45 | — | 43.0 |
| 20 | 80 | 13.9 | 15.0 | 6.0 | 5.0 | 0.04 | 2.9 | — | 44.5 |
| 10 | 90 | 15.6 | 16.0 | 6.6 | 0.15 | — | — | — | — |
| 5 | 95 | 15.7 | 16.0 | 5.6 | 0.1 | 0.0455 | — | 8.2 | 45.1 |
| 1 | 99 | 17.6 | — | 5.8 | — | — | — | — | 50.0 |

-continued

| Aqueous 1% (w/v) -PVA-HEC Mixtures | | Film Thickness Weight Technique[3] | Film Thickness by Draining Technique[4] | Drainage Time[4] | Dewetting Time[5] | Surface Viscosity[6] | Relative Viscosity[7] | Vertical Film Climbing Rate[8] | Surface Tension |
|---|---|---|---|---|---|---|---|---|---|
| %PVA(w/w)[1] | %HEC(w/w)[2] | μ | μ | min | hr | (poise) | (t/t₀) | | (dyne/cm.) |
| 0 | 100 | 10.0 | 8.0 | <0.1 | <0.1 | 0.052 | 3.7 | 4.9 | 59.0 |

[1]PVA - polyvinyl alcohol, Goshenol GL-05, supplied by Hercules Corp.
[2]HEC - hydroxyethylcellulose, Natrosol 250, supplied by DuPont Co.
[3]Film Thickness: Weight Technique
Take a clean Plexiglas (Polymethyl methacrylate) slide having dimensions 7.5 cm × 2.5 cm × 0.2 cm, and measure its dry weight on a Sartorius balance (accuracy 0.001 gm). Make a mark on the edge of the slide at a height of 5 cm from the bottom. The solution to be tested is taken in a beaker and is raised (at a constant speed of 1.0 cm/sec) so as to cover the Plexiglas slide up to the 5 cm mark. The total wetted area (if the solution does wet the Plexiglas surface) is 52 cm². Lower the beaker at the same speed. Blot excess solution from the bottom of the slide for 5 seconds using a piece of filter paper. Allow drainage for one minute and then measure the weight of the slide plus the attached solution. Calculate the weight of solution adhering to the Plexiglas. Then calculate the average film thickness $$= \frac{\text{Weight of adhering solution}}{52 \times \text{Density of solution}}$$

The average of 5 - 10 measurements is the reported value (S.D. = ± 5%).
[4]Film Thickness Using the SLFP
The instruments used was a Slit Lamp Fluorophotometer (SLFP) [Waltman, S. R., and Kaufman, H. E., Invest. Ophthalmol., 14 (12), 887 (1975)]. All solutions used in measurements made with the SLFP had a Sodium Fluorescein (water soluble Fluorescent dye) concentration of $5 \times 10^{-4}$ gm/ml. The procedure is identical to that described in the previous section. The solution is raised at a constant speed to wet 5 cm of the slide and then lowered at the same speed. The slit of light from the SLFP is focused at the mid point of the wetted area, 2.5 cm from the bottom of the slide, and fluorescent intensity recorded. The intensity after one minute of drainage is noted and the corresponding thickness calculated from a calibration curve. The average of two readings is taken. After lowering the solution from the slide, a continuous recording of the fluorescent intensity is made. The calibration curve shows a linear dependance between film thickness and fluorescent intensity for thickness in the range of 0 - 75 μm. The drainage time (td) is defined as the time elapsed before the film thickness (δ) reaches 5% its initial value ($\delta_o$).
[5]Dewetting Time
A clean Plexiglas slide (7.5 cm × 2.5 cm × 0.2 cm) was immersed in the solution being tested and allowed to soak for at least 24 hours so absorption equilibrium, if any, would be achieved. Such adsorption allows the solution to wet the low energy (critical surface tension = 38 - 40 dynes/cm) Plexiglas surface. The slide is then clamped to a horizontal bar which can move up and down (dipping) at the rate of 5 dips/minute. Excess solution was allowed to drain from the slide and the "dipping machine" was started. At the bottom of every downstroke, the slide dipped into a beaker containing 100 ml. isotonic saline. "Dewetting time" was defined as the dipping time required for the first dry spot to appear on the slide, indicating desorption of adsorbed molecules with consequent unwettability of the slide. It should be noted that each experiment was run for only five hours. Consequently a result of "5 hours" should be taken to indicate that the slide was still wettable at the end of five hours, and this value is therefore a lower limit of dewetting time for this solution.
[6]Surface Viscosity [Ref. Karam, J. App. Polymer Sci., 18, 1693-1709 (1974)]
Measurements of surface viscosity were carried out using a Knife Edge Surface Viscometer. A fixed amount of solution is pipetted into a cup that is mounted on a turntable capable of rotating at variable speeds. A circular knife edge bob, suspended from a torsion wire, is adjusted with the aid of leveling screws so it is centered with the cup. The bob is slowly lowered until its knife edge just touches the surface of the solution in the cup. The motor is started and the rotation speed of the turntable fixed. The rotation of the solution in the cup causes a deflection of the bob. This deflection from its rest position is measured with the aid of a telescope. The speed of the turntable (Ω) is changed to a new value and the deflection (θ) measured again. The corresponding surface viscosities are calculated from $$\eta_s = \frac{K(\theta - \theta_w)}{4 \pi w} \left( \frac{1}{R_b^2} - \frac{1}{R_c^2} \right) \text{ Newtonian}$$

$$\eta_s = \frac{K(\theta - \theta_0 - \theta_w)}{4 \pi w} \left( \frac{1}{R_b^2} - \frac{1}{R_c^2} \right) \text{ Binghum Plastic}$$

where
$\eta_S$ = surface viscosity in surface poise (s/p)
$\theta$ = angular deflection of bob for a given w
$\theta_w$ = corresponding deflection of bob for pure water - air surface
w = angular velocity
$R_b, R_c$ = Radii of bob and cup
K = Wire Torsion constant
The wire torsion constant, K, was determined by first measuring the period ($T_o$) of the chuck and dampening ring, then adding a mass of known moment of inertia (ΔI) and measuring a new period of oscillation ($T_1$). Then $$K = \frac{4 \pi^2 \Delta I}{T_1^2 - T_0^2}$$

All readings were taken at least twice and were reproducible to within 5%.
[7]Relative Viscosity
Relative viscosities were measured with a capillary viscometer of the Cannon-Fenske type. The size of the viscometer was either No. 25 or No. 50. The temperature was held constant at 25 ± 0.1C°. All measurements were repeated at least three times with excellent reproducibility.
[8]Benedetto et al, Investigative Ophthalmology 14, 887 (1975)

It is evident from the above results, that desirable film properties such as film thickness, drainage time, and dewetting are not directly related to solution viscosity, but rather are very sensitive to variations in the proportions of the hydroxyethylcellulose and polyvinyl alcohol. The aqueous compositions of this invention provide for a thick stable lachrymal film, as well as wetting and cushioning for contact lenses. In addition, the subject compositions can be used as vehicles for a wide variety of drugs. Illustrative drugs include epinephrine, norepinephrine, phenylephrine, atropine, scopolamine, benoxinate, sodium fluorescein, pilocarpine, dexamethasone phosphate, prednisolone, proparacaine, sodium sulfacetamide, sulfisoxazole, cyclopentolate, homatropine, rose bengal, tetracaine, polymyxin B, neomycin, gramicidin, dichlorphenamide, isofluorophate, demecarium bromide, chloramphenicol, napazoline, idoxuridine and carbachol. The concentration of the drugs will vary widely depending on the individual drug. The concentration will generally range from about 0.001 weight percent to 5 weight percent, more usually from about 0.002 weight percent to 2 weight percent of the ophthalmic solution. For individual drugs, concentrations will generally be in the range of about 0.001 to 1 weight percent, more usually from 0.005 to 1 weight percent. Antibiotics and steroids will generally range from about 0.05 to 1 weight percent while alkaloids, epinephrines and their derivatives will generally range from about 0.1 to 2 weight percent.

By employing the subject compositions as vehicles for drugs, a uniform stable film containing the drug is maintained for relatively long periods of time on the eye. Thus, greater effectiveness can be achieved with a wide variety of drugs.

Although the foregoing invention has been described in some detail by way of illustration and example for purposes of clarity of understanding, it will be obvious that certain changes and modifications may be practiced within the scope of the appended claims.

What is claimed is:

1. A method for the treatment of dry eye which comprises applying to the eye of a host having dry eye an aqueous solution containing from 0.1 to 10 weight percent of a polymer combination of hydroxyethylcellulose and polyvinyl alcohol of about 80 weight percent and about 20 weight percent respectively and has a viscosity of from 3,000 to 8,000 at a two weight percent aqueous solution, Brookfield viscosity, 25° C. and said polyvinyl alcohol has a viscosity of from about 1 to 20 at a 4% w/v solution, ASTM 882.

2. A method according to claim 1, wherein said aqueous composition has a pH in the range of about 5.5 to 8.5 and has from about 0.4 to 1.4 weight percent sodium chloride.

* * * * *